US010385290B2

(12) United States Patent
Berthier et al.

(10) Patent No.: US 10,385,290 B2
(45) Date of Patent: Aug. 20, 2019

(54) PROCESS FOR PREPARING POLYUREA MICROCAPSULES

(71) Applicant: Firmenich SA, Geneva (CH)

(72) Inventors: Damien Berthier, Geneva (CH); Marlène Jacquemond, Geneva (CH); Nicolas Paret, Geneva (CH); Lahoussine Ouali, Geneva (CH)

(73) Assignee: FIRMENICH SA, Geneva (CH)

( * ) Notice: Subject to any disclaimer, the term of this patent is extended or adjusted under 35 U.S.C. 154(b) by 0 days.

(21) Appl. No.: 15/564,817

(22) PCT Filed: Apr. 6, 2016

(86) PCT No.: PCT/EP2016/057527
§ 371 (c)(1),
(2) Date: Oct. 6, 2017

(87) PCT Pub. No.: WO2016/162381
PCT Pub. Date: Oct. 13, 2016

(65) Prior Publication Data
US 2018/0112152 A1    Apr. 26, 2018

(30) Foreign Application Priority Data
Apr. 7, 2015 (EP) .................... 15162653

(51) Int. Cl.
| | |
|---|---|
| *A61K 8/11* | (2006.01) |
| *A61K 8/40* | (2006.01) |
| *A61Q 15/00* | (2006.01) |
| *A61Q 19/00* | (2006.01) |
| *A61Q 19/10* | (2006.01) |
| *C11B 9/00* | (2006.01) |
| *B01J 13/16* | (2006.01) |
| *C11D 3/50* | (2006.01) |
| *A61Q 5/12* | (2006.01) |
| *C11D 3/00* | (2006.01) |

(52) U.S. Cl.
CPC .............. *C11B 9/0061* (2013.01); *A61K 8/11* (2013.01); *A61K 8/40* (2013.01); *A61Q 5/12* (2013.01); *A61Q 15/00* (2013.01); *A61Q 19/00* (2013.01); *A61Q 19/10* (2013.01); *B01J 13/16* (2013.01); *C11B 9/00* (2013.01); *C11D 3/001* (2013.01); *C11D 3/505* (2013.01)

(58) Field of Classification Search
CPC . A61K 8/11; A61K 8/40; A61Q 15/00; A61Q 19/00; A61Q 19/10
See application file for complete search history.

(56) References Cited

U.S. PATENT DOCUMENTS

| | | | |
|---|---|---|---|
| 5,225,118 | A | 7/1993 | Juang et al. |
| 2007/0202063 | A1 | 8/2007 | Dihora et al. |
| 2011/0071064 | A1* | 3/2011 | Lei |
| 2013/0313734 | A1 | 11/2013 | Yao et al. |
| 2013/0330292 | A1* | 12/2013 | Lei |
| 2013/0337023 | A1 | 12/2013 | Lei et al. |

FOREIGN PATENT DOCUMENTS

| | | | |
|---|---|---|---|
| EP | 1741775 | B1 | 4/2009 |
| GB | 2432843 | A | 6/2007 |
| GB | 2432850 | A | 6/2007 |
| GB | 2432851 | A | 6/2007 |
| GB | 2432852 | A | 6/2007 |
| WO | WO2005054422 | A1 | 6/2005 |
| WO | 2007/062833 | A1 | 6/2007 |
| WO | WO2007062733 | A1 | 6/2007 |
| WO | WO2008016684 | A1 | 2/2008 |
| WO | WO2011154893 | A1 | 12/2011 |
| WO | WO2013000587 | A1 | 1/2013 |
| WO | 2013/000587 | A1 * | 2/2013 |
| WO | WO2015023961 | A1 | 2/2015 |

OTHER PUBLICATIONS

International Search Report and Written Opinion, application PCT/EP2016/057527 dated Jun. 23, 2016.

* cited by examiner

*Primary Examiner* — Alma Pipic
(74) *Attorney, Agent, or Firm* — Winston & Strawn LLP (57) ABSTRACT

The present invention relates to a process for producing perfume-containing microcapsules with improved olfactive performance by using at least one aromatic polyisocyanate with a specific mixture of polyamines. Microcapsules obtainable by such a process and perfuming compositions or the consumer products comprising these microcapsules are also objects of the invention. In particular, the microcapsules can be used in home or personal care products.

17 Claims, 3 Drawing Sheets

PROCESS FOR PREPARING POLYUREA MICROCAPSULES

This application is a 371 filing of International Patent Application PCT/EP2016/057527 filed Apr. 6, 2016, which claims the benefit of European patent application No. 15162653.8 filed Apr. 7, 2015.

TECHNICAL FIELD

The present invention relates to the field of delivery systems. More particularly, the present invention relates to a process for producing oil-containing core-shell microcapsules, in particular perfume-containing microcapsules with improved olfactive performance. Microcapsules obtainable by such a process and perfuming compositions or the consumer products comprising these microcapsules are also objects of the invention. In particular, the microcapsules can be used in home or personal care products.

BACKGROUND

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

A key requirement from the industry regarding these systems is to provide a good olfactive experience in a challenging medium such as a perfumed consumer product. This means, on one hand, that efficient delivery systems should survive in challenging consumer product bases containing high level of surfactant without physically dissociating or degrading. This performance corresponds to the stability of the delivery systems. On the other hand, another success criteria for delivery systems encapsulating actives such as a perfume consists of the efficiency in releasing the perfume referred to as olfactive performance and related to the way capsules are breaking during use of the consumer product.

Aminoplast microcapsules formed of a melamine-formaldehyde resin have been largely used to encapsulate hydrophobic actives, thus protecting said actives and providing their controlled release. Although capsules such as aminoplast ones afford good olfactive performance, they suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as polyamines and polyisocyanates, has been described as a way to improve stability of microcapsules. WO 2011/154893 discloses for instance a process for the preparation of polyurea microcapsules using a combination of aromatic and aliphatic polyisocyanates in specific relative concentrations and wherein the most preferred polyamine is selected from the group consisting of guanidine, water-soluble guanidine salts and N,N'-bis-(3-aminopropyl)-ethylenediamine. Compared to aminoplast, polyurea-based microcapsules present the additional advantage of being free from melamine-formaldehyde. However, these capsules are not always satisfactory in terms of mechanical properties as that are less friable, which can negatively impact their olfactive performance represented by the odor intensity perceived during handling and after intentional breakage e.g. by rubbing.

A solution to the above-mentioned problem has been proposed in WO 2013/000587. In particular, an improvement of the breakability of the polyurea microcapsules and so of the olfactive performance of the polyurea microcapsules while maintaining a satisfying stability in consumer product has been described by replacing guanidine and guanidine salts, commonly used as polyamines in such capsules, by 3,5-diamino-1,2,4-triazole.

However, there is still a need to provide improved capsules to those known from the prior art, that would be free of melamine-formaldehyde and at the same time olfactively more performing than existing polyurea-based capsules but also as stable as existing melamine-formaldehyde and/or polyurea-based capsules in challenging media such as surfactant-based consumer products.

The present invention provides a solution to the above mentioned problems through a process wherein the shell of microcapsules is formed by the reaction between at least one aromatic polyisocyanate and a mixture of two polyamines. The use of two polyamines to form microcapsules has been reported in US2013/313734. Said document points out the importance to add first a guanidine aqueous solution to form a pre-microcapsules and then add a second polyamine.

SUMMARY OF THE INVENTION

The invention relates to a novel process to prepare microcapsules, which allows improving the olfactive performance of the obtained microcapsules. Unexpectedly the use of at least one aromatic polyisocyanate with a mixture of two polyamines in particular ratios leads to microcapsules with improved breakability.

A first object of the present invention is therefore a process for the preparation of polyurea microcapsules comprising the following steps:
a) dissolving at least one aromatic polyisocyanate having at least two isocyanate groups, in an oil-based core material, preferably a perfume-containing oil to form an oil phase;
b) dispersing the oil phase obtained in step a) into an aqueous solution comprising a emulsifier to form an oil-in-water emulsion;
c) adding to the oil-in-water emulsion obtained in step b) a mixture of two polyamines in a respective molar ratio comprised between 95:5 to 5:95, to form a microcapsule slurry;
d) optionally drying the slurry.

A second object of the present invention consists of polyurea core-shell microcapsules obtainable by the process as defined above comprising
a) an oil-based core preferably comprising a perfume;
b) a shell formed by the interfacial polymerization of at least one aromatic polyisocyante having at least two isocyanate groups and a mixture of two polyamines in a respective molar ratio comprised between 95:5 to 5:95; and
c) an emulsifier on the surface of the shell.

A third object of the present invention is a perfuming composition comprising a) as perfuming ingredient, polyurea microcapsules as defined above;
b) at least one ingredient selected from the group consisting of a perfumery carrier, a perfumery co-ingredient and a mixture thereof;
c) optionally at least one perfumery adjuvant.

Another object of the present invention is a perfuming consumer product comprising as perfuming ingredient, the polyurea microcapsules or the perfuming composition defined above.

A last object of the present invention is the use of polyurea microcapsules defined above or of a perfuming composition comprising said microcapsules in a consumer product to deliver perfume onto a surface, characterized in that said surface is treated with said polyurea microcapsules or perfuming composition.

DETAILED DESCRIPTION OF THE INVENTION

The process of this invention advantageously allows obtaining polyurea microcapsules with superior breakability which consequently improves the performance of capsules in terms of active ingredients release, in particular perfume release. This novel process leads to the formation of core-shell microcapsules wherein the co-polymer constituting the wall in made from interfacial polymerization between at least one aromatic polyisocyanate and a mixture of two polyamines. More particularly, It has been found that the use of at least one aromatic polyisocyanate in combination with a mixture of two polyamines in a respective molar ratio comprised between 95:5 to 5:95 advantageously increases the brittleness of the microcapsules and so the olfactive performance.

The present invention advantageously bring a new solution in the polyurea capsule technical field as the specific wall structure provides unexpected performance with regards to mechanical properties of the capsules (friability).

Therefore, a first object of the present invention is a process for the preparation of polyurea microcapsules comprising the following steps:
a) dissolving at least one aromatic polyisocyanate having at least two isocyanate groups, in an oil-based core material, preferably a perfume-containing oil to form an oil phase;
b) dispersing the oil phase obtained in step a) into an aqueous solution comprising a emulsifier to form an oil-in-water emulsion;
c) adding to the oil-in-water emulsion obtained in step b) a mixture of two polyamines in a respective molar ratio comprised between 95:5 to 5:95, to form a microcapsule slurry;
d) optionally drying the slurry.

In the first step of the process according to the invention, at least one aromatic polyisocyanate having at least two isocyanate groups is dissolved in an oil-based core material to form an oil phase.

By the terms "oil-based core material" it is meant a liquid or a solution, at 20° C. and 1 atm of pressure, which is capable of bringing a benefit or effect into its surrounding environment by the presence of an active agent such as, in particular, a perfuming, flavoring, cosmetic, skin caring, malodor counteracting, bactericide, fungicide, pharmaceutical or agrochemical ingredient, nutraceutical, biocide active, a diagnostic agent and/or an insect control agent.

Said oil-based core material can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient, nutraceutical, biocide active, a diagnostic agent and/or an insect control agent.

Preferably, said oil-based core material can be composed of a single compound or of a mixture of compounds wherein at least one of the said compounds possesses at least one property which renders it useful as perfuming, flavoring, cosmetic, nutraceutical, biocide active, and/or an insect control agent. Even more preferably, said oil-based core material can be composed of a single compound or of a mixture of compounds wherein at least one of the said compounds possesses at least one property which renders it useful as perfuming ingredient.

According to another preferred embodiment, the oil-based core material can be composed of a mixture of compounds comprising at least one perfuming ingredient and at least one another active agent possessing at least one property which renders it useful as flavoring, cosmetic, nutraceutical, biocide active, and/or an insect control agent.

According to another particular embodiment, the oil-based core material may be composed of a single compound or of a mixture of compounds wherein at least one of the said compounds possesses at least one property which renders it useful as cosmetic, nutraceutical, biocide active, and/or an insect control agent provided that no perfuming ingredient is present.

Practically, the invention is carried out exactly in the same manner, independently of the exact nature of the active agent present in the oil phase. Therefore, it is understood that, even if the invention will be further illustrated herein below with a specific reference to "perfuming" ingredients, the below embodiments are also applicable to other active agent-containing oils (i.e. it is possible to replace the expression "perfuming" with "flavoring", "cosmetic", "skin caring", "malodor counteracting", "bactericide", "fungicide", "pharmaceutical", "agrochemical", "diagnostic agent", "nutraceuticals", "biocide active", "insect control agent" for instance).

By "perfume" (or also "perfume oil") it is meant here a perfume that is liquid at about 20° C. According to any one of the above invention embodiments said perfume oil in which the polyisocyanate is dissolved in step a) can be a perfuming ingredient alone or a mixture of ingredients. By "perfuming ingredient" it is meant here a compound, which is used in a perfuming preparation or a composition to impart a hedonic effect. In other words such an ingredient, to be considered as being a perfuming one, must be recognized by a person skilled in the art as being able to primary impart or modify in a positive or pleasant way the odor of a composition, and not just as having an odor. The perfuming ingredient may also impart a pleasant odor by masking or neutralizing unpleasant odors. In other words such an ingredient, to be considered as being a perfuming one, must be able to at least impart or modify in a positive or pleasant way the odor or taste of a composition, and not just as having an odor or taste. Said ingredient can on top of their primary purpose provides secondary benefits, including but not limited to malodour counteraction, antimicrobial effect, microbial stability, food preservation, sanitization, insect repellence or taste-masking.

The nature and type of the perfuming ingredients do not warrant a more detailed description here, which in any case would not be exhaustive, the skilled person being able to select them on the basis of his general knowledge and according to intended use or application and the desired organoleptic effect. In general terms, these perfuming ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredient(s) to be encapsulated may be dissolved in a solvent of current use in the perfume industry thus the core of the capsule might be pure perfuming ingredients or a mixture of perfuming ingredients in an adequate hydrophobic solvent. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn®. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:
  Group 1: perfuming ingredients comprising a cyclohexane, cyclohexene, cyclohexanone or cyclohexenone ring substituted with at least one linear or branched $C_1$ to $C_4$ alkyl or alkenyl substituent;
  Group 2: perfuming ingredients comprising a cyclopentane, cyclopentene, cyclopentanone or cyclopentenone ring substituted with at least one linear or branched $C_4$ to $C_8$ alkyl or alkenyl substituent;
  Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;
  Group 4: perfuming ingredients comprising at least two fused or linked $C_5$ and/or $C_6$ rings;
  Group 5: perfuming ingredients comprising a camphor-like ring structure;
  Group 6: perfuming ingredients comprising at least one $C_7$ to $C_{20}$ ring structure;
  Group 7: perfuming ingredients having a log P value above 3.5 and comprising at least one tert-butyl or at least one trichloromethyl substituent;
Examples of ingredients from each of these groups are:
Group 1: 2,4-dimethyl-3-cyclohexene-1-carbaldehyde (origin: Firmenich SA, Geneva, Switzerland), isocyclocitral, menthone, isomenthone, Romascone® (methyl 2,2-dimethyl-6-methylene-1-cyclohexanecarboxylate, origin: Firmenich SA, Geneva, Switzerland), nerone, terpineol, dihydroterpineol, terpenyl acetate, dihydroterpenyl acetate, dipentene, eucalyptol, hexylate, rose oxide, Perycorolle® ((S)-1,8-p-menthadiene-7-ol, origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, Doremox® (tetrahydro-4-methyl-2-phenyl-2H-pyran, origin: Firmenich SA, Geneva, Switzerland), cyclohexyl acetate, cyclanol acetate, Fructalate® (1,4-cyclohexane diethyldicarboxylate, origin: Firmenich SA, Geneva, Switzerland), Koumalactone® ((3ARS,6SR,7ASR)-perhydro-3,6-dimethyl-benzo[B]furan-2-one, origin: Firmenich SA, Geneva, Switzerland), Natactone® ((6R)-perhydro-3,6-dimethyl-benzo[B]furan-2-one, origin: Firmenich SA, Geneva, Switzerland), 2,4,6-trimethyl-4-phenyl-1,3-dioxane, 2,4,6-trimethyl-3-cyclohexene-1-carbaldehyde;
Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3-cyclopenten-1'-yl)-2-buten-1-ol (origin: Firmenich SA, Geneva, Switzerland), Polysantol® ((1'R,E)-3,3-dimethyl-5-(2',2',3'-trimethyl-3'-cyclopenten-1'-yl)-4-penten-2-ol, origin: Firmenich SA, Geneva, Switzerland), fleuramone, Hedione® HC (methyl-cis-3-oxo-2-pentyl-1-cyclopentane acetate, origin: Firmenich SA, Geneva, Switzerland), Veloutone® (2,2,5-Trimethyl-5-pentyl-1-cyclopentanone, origin: Firmenich SA, Geneva, Switzerland), Nirvanol® (3,3-dimethyl-5-(2,2,3-trimethyl-3-cyclopenten-1-yl)-4-penten-2-ol, origin: Firmenich SA, Geneva, Switzerland), 3-methyl-5-(2,2,3-trimethyl-3-cyclopenten-1-yl)-2-pentanol (origin, Givaudan SA, Vernier, Switzerland);
Group 3: damascones, Neobutenone® (1-(5,5-dimethyl-1-cyclohexen-1-yl)-4-penten-1-one, origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, Dynascone® (mixture of 1-(5,5-dimethyl-1-cyclohexen-1-yl)-4-penten-1-one and 1-(3,3-dimethyl-1-cyclohexen-1-yl)-4-penten-1-one, origin: Firmenich SA, Geneva, Switzerland), Dorinone® beta (1-(2,6,6-trimethyl-1-cyclohexen-1-yl)-2-buten-1-one, origin: Firmenich SA, Geneva, Switzerland), Romandolide® ((1S,1'R)-[1-(3',3'-Dimethyl-1'-cyclohexyl)ethoxycarbonyl]methyl propanoate, origin: Firmenich SA, Geneva, Switzerland), 2-tert-butyl-1-cyclohexyl acetate (origin: International Flavors and Fragrances, USA), Limbanol® (1-(2,2,3,6-tetramethyl-cyclohexyl)-3-hexanol, origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, Lorysia® (4-(1,1-dimethylethyl)-1-cyclohexyl acetate, origin: Firmenich SA, Geneva, Switzerland), 8-methoxy-1-p-menthene, Helvetolide® ((1S,1'R)-2-[1-(3',3'-dimethyl-1'-cyclohexyl) ethoxy]-2-methylpropyl propanoate, origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), Verdylate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR, 10RS) isomer, 6-ethyl-2,10,10-trimethyl-1-oxaspiro [4.5]deca-3,6-diene, 1,2,3,5,6,7-hexahydro-1,1,2,3,3-pentamethyl-4-indenone (origin: International Flavors and Fragrances, USA), Hivernal® (a mixture of 3-(3, 3-dimethyl-5-indanyl)propanal and 3-(1,1-dimethyl-5-indanyl)propanal, origin: Firmenich SA, Geneva, Switzerland), Rhubofix® (3',4-dimethyl-tricyclo[6.2.1.0(2, 7)]undec-4-ene-9-spiro-2'-oxirane, origin: Firmenich SA, Geneva, Switzerland), 9/10-ethyldiene-3-oxatricyclo[6.2.1.0(2,7)]undecane, Polywood® (perhydro-5,5, 8A-trimethyl-2-naphthalenyl acetate, origin: Firmenich SA, Geneva, Switzerland), octalynol, Cetalox® (dodecahydro-3a,6,6,9a-tetramethyl-naphtho[2,1-b]furan, origin: Firmenich SA, Geneva, Switzerland), tricyclo [5.2.1.0(2,6)]dec-3-en-8-yl acetate and tricyclo[5.2.1.0 (2,6)]dec-4-en-8-yl acetate as well as tricyclo[5.2.1.0 (2,6)]dec-3-en-8-yl propanoate and tricyclo[5.2.1.0(2, 6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, camphopinene, cedramber (8-methoxy-2,6,6,8-tetramethyl-tricyclo[5.3.1.0(1,5)]undecane, origin: Firmenich SA, Geneva, Switzerland), cedrene, cedrenol, cedrol, Florex® (mixture of 9-ethylidene-3-oxatricyclo[6.2.1.0 (2,7)]undecan-4-one and 10-ethylidene-3-oxatricyclo [6.2.1.0(2,7)]undecan-4-one, origin: Firmenich SA, Geneva, Switzerland), 3-methoxy-7,7-dimethyl-10-methylene-bicyclo[4.3.1]decane (origin: Firmenich SA, Geneva, Switzerland);

Group 6: Cedroxyde® (trimethyl-13-oxabicyclo-[10.1.0]-trideca-4,8-diene, origin: Firmenich SA, Geneva, Switzerland), Ambrettolide LG ((E)-9-hexadecen-16-olide, origin: Firmenich SA, Geneva, Switzerland), Habanolide® (pentadecenolide, origin: Firmenich SA, Geneva, Switzerland), muscenone (3-methyl-(4/5)-cyclopentadecenone, origin: Firmenich SA, Geneva, Switzerland), muscone (origin: Firmenich SA, Geneva, Switzerland), Exaltolide® (pentadecanolide, origin: Firmenich SA, Geneva, Switzerland), Exaltone® (cyclopentadecanone, origin: Firmenich SA, Geneva, Switzerland), (1-ethoxyethoxy)cyclododecane (origin: Firmenich SA, Geneva, Switzerland), Astrotone, 4,8-cyclododecadien-1-one;

Group 7: Lilial® (origin: Givaudan SA, Vernier, Switzerland), rosinol.

Preferably, the perfume in which the polyisocyanate is dissolved comprises at least 30%, preferably at least 50%, more preferably at least 60% of ingredients selected from Groups 1 to 7, as defined above. More preferably said perfuming composition comprises at least 30%, preferably at least 50% of ingredients from Groups 3 to 7, as defined above. Most preferably said composition comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the process of the invention contains less than 10% of its own weight of primary alcohols, less than 15% of its own weight of secondary alcohols and less than 20% of its own weight of tertiary alcohols. Advantageously, the perfume used in the process of the invention does not contain any primary alcohols and contains less than 15% of secondary and tertiary alcohols. Such limited amounts of alcohols have the advantage of reducing the amount of isocyanate functional groups reacting with the perfume.

According to preferred embodiments of the invention, there is used an amount of between 10 and 60%, more preferably between 20 and 50% of perfume in the process of the invention, these percentages being defined by weight relative to the total weight of the obtained microcapsules.

The at least one aromatic polyisocyanate used in the process of the invention contains at least two isocyanate groups, preferably at least three isocyanate groups. The mixture of two polyamines added in step c) of the process will react with those functional groups by interfacial polymerization to form the core-shell structure of the capsules. Following the numbers of functional groups, an optimal reticulation or network of the capsules wall will be achieved, providing thus microcapsules exhibiting a good olfactive performance, as well as an improved stability in the consumer product. Low volatility polyisocyanate molcules are preferred because of their low toxicity.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the at least one aromatic polyisocyanate comprises trimethylol propane-adduct of xylylene diisocyanate.

According to a particular embodiment, the at least one aromatic polyisocyanate may be combined with an aliphatic polyisocyanate. In the case of mixtures of polyisocyanates, each member of the mixture has at least two isocyanate functional groups.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

Preferably the at least one aromatic polyisocyanate is added in an amount comprised between 1 and 30% by weight, relative to the total weight of the solution obtained in step a), more preferably between 2 and 20% by weight, relative to the total weight of the solution obtained in step a).

According to a particular embodiment of the invention, the oil phase of step a) is devoid of any aliphatic polyisocyanate. Preferably, the at least one aromatic polyisocyanates consists of trimethylol propane-adduct of xylylene diisocyanate.

In step b) of the process of the present invention, the oil phase is dispersed into an aqueous solution comprising an emulsifier to form a water-in-oil emulsion.

The term "emulsion" is meant to designate here the fact that the oil phase obtained in step a) is dispersed in an aqueous solution. The term "emulsion" is therefore understood as emulsion or dispersion. The presence of an emulsifier in the aqueous solution allows the stabilization of the oil droplets therein. In the present invention a colloidal stabilizer could be used as emulsifier. The emulsion may be prepared by high shear mixing and adjusted to the desired droplet size. The droplet size can be checked with light scattering measurements or microscopy. This procedure does not require a more detailed description here as it is well known to a skilled person in the art.

Non limiting examples of emulsifier include polyvinyl alcohol, polyvinypyrrolidone, cellulose derivatives (such as hydroxyethyl cellulose), polyethylene oxide, copolymers of polyethylene oxide and polyethylene or polypropylene oxide, copolymers of acrylamide and acrylic acid, copolymer of vinylpyrrolidone and of a quaternized vinylimidazol such as those sold under the trade name Luviquat® (commercially available from BASF, sodium dodecyl sulfate or Stepantex® (commercially available from Stepan), diblock copolymers of polyethylene oxide and polyethylene or polypropylene oxide. Preferably, the emulsifier used in the process of the invention is polyvinyl alcohol (such as that sold by Kuraray under the trade name Mowiol® 18-88) or polyvinypyrrolidone. Even more preferably, the emulsifier used in the process of the invention is polyvinyl alcohol (such as that sold by Kuraray under the trade name Mowiol® 18-88).

Preferably the emulsifier is added in an amount comprised between 0.1 and 10% by weight, relative to the total weight of the of the obtained microcapsules slurry and more preferably between 0.3 and 1% by weight, relative to the total weight of the obtained microcapsules slurry.

In step c) of the process of the invention, a mixture of two polyamines is used in a respective molar ratio comprised between 95:5 to 5:95.

Preferably said polyamines of the mixture of two polyamines are selected from the group consisting of 1,2-diaminopropane, 1,2-diaminoethane, diethylenetriamine, guanidine, melamine, tris-(2-aminoethyl)amine, N,N'-bis(3-aminopropyl)-ethylenediamine, N,N,N',N'-tetrakis(3-aminopropyl)-1,4-butanediamine and 3,5-diamino-1,2,4-triazole.

More preferably, the polyamines are selected from the group consisting of guanidine, melamine, 3,5-diamino-1,2,4-triazole, tris-(2-aminoethyl)amine, N,N'-bis(3-aminopropyl)ethylenediamine and N,N,N',N'-tetrakis(3-aminopropyl)-1,4-butanediamine. Even more preferably, the mixture of two polyamines comprises 3,5-diamino-1,2,4-triazole. Most preferably, the mixture of two polyamines consists of guanidine and 3,5-diamino-1,2,4-triazole.

Preferably, the respective molar ratio of guanidine and 3,5-diamino-1,2,4-triazole is comprised between 45:55 to 5:95, more preferably between 35:65 to 15:85, even more preferably between 30:70 to 20:80 or between 28:72 to 10:90.

In the context of the invention, the term "guanidine" encompasses also water soluble guanidine salts. By "water soluble guanidine salt" it is meant a salt soluble in water and resulting from the reaction of guanidine with an acid. One example of such salts is guanidine carbonate.

The polyurea wall of the microcapsules is the result of the interfacial polymerisation between the polyisocyanate dissolved in step a) and the mixture of two polyamines added in step c).

The amount of mixture of two polyamines used is typically adjusted so that, for each mole of isocyanate group dissolved in the perfume of step a), there is added from 0.5 to 3 moles of amine groups in step c). Preferably, for each mole of isocyanate group dissolved in the perfume in step a), 1 to 3, more preferably 1 to 2 moles of amine groups are added in step c).

No specific action is required to induce the polymerisation between the polyisocyanates and the two polyamines. The reaction starts immediately after adding the polyamine mixture. Preferably the reaction is maintained for 2 to 15 hours, more preferably for 2 to 10 hours.

The specific composition of the wall of the capsule is key in obtaining microcapsules that are at the fine balance between release (mechanical properties) and retention (stability) so as to achieve satisfactory release of fragrances, once the capsules are placed on textiles or other substrates, while showing the desired stability in the end product base (e.g. counteracts efficiently the extraction of the perfume by the surfactants of the consumer product). The choice of the aromatic polyisocyanate and of the two polyamines added simultaneously, among the ones mentioned above, and the specific molar ratio between the two polyamines, enable the fine tuning of the mechanical properties and stability of the capsules.

In an optional step of the process of the invention, the microcapsules are washed via centrifugation and re-suspension several times. In another optional step, the microcapsules can be isolated from the slurry that is obtained from the process described. According to a particular embodiment, the capsule slurry obtained by the above-mentioned processes can further be dried. Any drying method known to a skilled person in the art can be used including, but not limited to fluidized bed or spray-drying tower with co-current or counter current air streams with atomizing devices of different configuration, such as two-fluid nozzles, rotary nozzles or ultrasonic nozzles. In particular the slurry may be spray-dried preferably in the presence of a polymeric carrier material such as polyvinyl acetate, polyvinyl alcohol, dextrines, maltodextrines, glucose syrups, natural or modified starch, vegetable gums, gum acacia, pectins, xanthanes, alginates, carragenans or cellulose derivatives to provide microcapsules in a powder form. A broad range of suitable spray drying configurations is available from companies like GEA-Niro (Denmark).

According to a particular embodiment, the capsule slurry obtained by the above-mentioned processes can further be mixed with a thermoplastic carrier to be extruded by any extrusion method known to a skilled person such as, but not limited to, spheronization, gear-pump, piston extrusion, single screw extrusion, twin-screw co-rotating extrusion, twin-screw counter rotating extrusion. Twin-screw extruders can have different screw configurations to get mixing zones, melting zones, homogenizing zones or venting zones and the like as is conventionally known in the art. The resulting molten mass embedding the capsules of the present invention can be further processed to be granulated by any methods including but not limited to quenching, grinding, die-face pelletization, molding. A broad range of suitable extrusion configurations is available from companies like Brabender or Coperion (Germany). By the term "thermoplastic carrier", it is meant the normal meaning understood by a person skilled in the art, i.e. that a thermoplastic carrier is a material which becomes soft above a certain temperature and becomes hard when cool. When the material is in a soft state, it could be shaped. This material could be heated several times without losing its thermoplastic property.

Another object of the present invention is a polyurea core-shell microcapsule obtainable by the process of any of the above-described embodiments comprising
  a) an oil-based core preferably comprising a perfume;
  b) a shell formed by the interfacial polymerization of at least one aromatic polyisocyante and the mixture of two polyamines in a respective molar ratio comprised between 95:5 to 5:95; and
  c) an emulsifier on the surface of the shell.

The use of at least one aromatic polyisocyanate with a mixture of two polyamines in said ratio to form the wall of the microcapsules following the process of the present invention, in particular with the simultaneous addition of both polyamines, provides capsules showing very good performance in terms of stability in challenging medium and unexpectedly superior mechanical properties than capsules from the prior art which translate into better odor performance.

According to a particular embodiment of the invention, the glass transition temperature of the copolymer constituting the wall of the capsules is superior to room temperature.

The microcapsules obtained have an average diameter (d(v, 0.5)) comprised between 1 and 100 μm, preferably comprised between 1 and 50 μm, more preferably comprised between 5 and 35 μm and even more preferably between 5 and 25 μm. In the present context, "average diameter" refers to the arithmetic mean.

The at least one aromatic polyisocyanate, the oil-based core preferably comprising perfume, the emulsifier, and the mixture of two polymaines, as well as their respective amounts in the capsules, are as defined above in any embodiment related to the process of the invention for the preparation of the microcapsules.

The microcapsules of the present invention can comprise other optional ingredients such as antioxidants, deposition aids, antimicrobial agents or antifoaming agents.

The microcapsules of the invention can be advantageously used for the controlled release of active agents and preferably of the encapsulated perfume. It is therefore particularly appreciated to include these microcapsules as perfuming ingredient in a perfuming composition or in a perfumed consumer product. The invention also relates to methods of perfuming via the use of the microcapsules of the invention.

Therefore, another object of the present invention is a perfuming composition comprising:
  a) as perfuming ingredient, polyurea microcapsules as defined above;
  b) at least one ingredient selected from the group consisting of a perfumery carrier, a perfumery co-ingredient and a mixture thereof; and
  c) optionally at least one perfumery adjuvant.

By "perfumery carrier" we mean here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

The term "perfumery co-ingredient" is equivalent to perfuming ingredient defined above.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of the invention's microcapsules as defined above and at least one perfumery carrier represents a particular embodiment of the invention.

Furthermore, microcapsules as defined above or a perfuming composition comprising such microcapsules can also be advantageously used in all the fields of modern perfumery, i.e. fine or functional perfumery, to prevent the malodor formation and to positively impart or modify the odor of a consumer product and into which said microcapsules as defined above are added.

As shown in the examples below, the polyurea microcapsules obtained by the process of the invention provide particularly good olfactive performance. They provide a controlled or triggered release of the encapsulated perfume, said perfume being slowly released from the microcapsules, thus considerably improving the perfume long-lastingness and intensity.

Consequently, another object of the present invention is represented by a perfuming consumer product comprising, as perfuming ingredient, microcapsules as defined above.

The invention's microcapsules can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's microcapsules. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent or refresher; or a malodor neutralizing sanitary product; or a pet product in the form of absorbent pads, litters, cleansers and refreshing and perfuming sprays and products.

The capsules slurry obtained in the process of the invention may be used as such to perfume the consumer products, in which case the reaction mixture is directly added to a consumer product as defined in any of the above embodiments. Alternatively, the microcapsules obtained in the process of the invention may be isolated from the reaction mixture before being incorporated into the consumer product. Similarly, the reaction mixture comprising the microcapsules of the invention may be mixed with or sprayed onto a dry, powdered product, such as a washing powder or powdered detergent or the microcapsules may be dried and added to these products in solid form. The microcapsules may for example be spray-dried as defined above.

As anticipated above, the invention's composition can be advantageously used for bringing a benefit to consumer products, such as its perfuming effect. Because some of the compounds of the oil phase described above can also have flavoring, cosmetic, skin caring, malodor counteracting, bactericide, fungicide, pharmaceutical, agrochemical, insect control, biocide, neutraceutical properties, it is evident that the invention's microcapsules can also be used in formulations serving for flavoring, cosmetic, skin caring, malodor counteracting, bactericide, fungicide, pharmaceutical, agrochemical, insect control, neutraceutical, biocide purposes. Indeed, said microcapsules, possess several other properties that make them particularly suitable for this purpose.

The proportions in which the microcapsules according to the invention can be incorporated into the various aforementioned articles or compositions vary within a wide range of values. These values are dependent on the nature of the article to be perfumed and on the desired organoleptic effect as well as the nature of the co-ingredients in a given base when the microcapsules according to the invention are mixed with perfuming co-ingredients, solvents or additives commonly used in the art.

For example, in the case of perfuming compositions, typical concentrations are in the order of 0.001% to 5% by weight, or even more, of the microcapsules of the invention based on the weight of the composition into which they are incorporated. Concentrations lower than these, such as in the order of 0.01% to 1% by weight, can be used when these microcapsules are incorporated into perfumed articles, percentage being relative to the weight of the article.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

A last object of the present invention is the use polyurea microcapsules as defined above or perfuming composition comprising said microcapsules in a consumer product to deliver perfumes onto a surface or in the airborne, characterized in that said surface or airbone is treated with said polyurea microcapsules or perfuming composition.

EXAMPLES

The following non limiting examples are further illustrative of the present invention embodiments, and further demonstrate the advantages of the invention.

Abbreviations have the usual meaning in the art and the temperatures are indicated in degrees centigrade (° C.).

Example 1

Preparation of Polyurea Microcapsules According to the Present Invention and Control Microcapsules
General Procedure Polyisocyanate was diluted into a perfume oil (Table 1) to form an oil phase. Polyvinyl alcohol (Mowiol® 18-88, trademark from Kuraray) was diluted in water. The oil phase and the aqueous PVOH solution were mixed together, and then dispersed with Ultra Turrax for 3 min at 24 000 rpm. The emulsion was put into a 250 mL glass double-jacketed reactor and agitated at 350 rpm at room temperature. A solution of guanidine carbonate and 3,5-diamino-1,2,4-triazole (known also under name guanazole) in water was added dropwise into the emulsion for 1 h. Then, the temperature of the reaction mixture was slowly increased from room temperature to 70° C. in 4 times every 15 minutes (RT; 40° C.; 50° C.; 60° C.; 70° C.) and then kept at 70° C. for 2 h. Finally, the agitation was reduced at 100 rpm and the dispersion was cooled down to room temperature.

TABLE 1

| perfume oil composition | |
| --- | --- |
| Raw material | wt % |
| Romascone ®[a] | 20 |
| Verdox ™[b] | 20 |

TABLE 1-continued

| perfume oil composition | |
| --- | --- |
| Raw material | wt % |
| Lorysia ®[c] | 20 |
| 3-(4-isopropylphenyl)-2-methylpropanal | 20 |
| Salicynile ®[d] | 20 |

[a] Methyl 2,2-dimethyl-6-methylene-1-cyclohexanecarboxylate, origin: Firmenich SA, Geneva, Switzerland
[b] 2-tert-butyl-1-cyclohexyl acetate, origin and trade mark owned by International Flavors & Fragrances, USA
[c] 4-(1,1-diméthyléthyl)-1-cyclohexyl acetate, origin: Firmenich SA, Geneva, Switzerland
[d] (2Z)-2-phenyl-2-hexenenitrile, origin: Firmenich SA, Geneva, Switzerland Capsules a to M Polyurea microcapsules A to F according to the invention and control microcapsules G to M were prepared following the general procedure with the following ingredients:

TABLE 2

| | Composition of Capsules A to F | | | | | |
| --- | --- | --- | --- | --- | --- | --- |
| Ingredient | Capsules A Amount (wt %) | Capsules B Amount (wt %) | Capsules C Amount (wt %) | Capsules D Amount (wt %) | Capsules E Amount (wt %) | Capsules F Amount (wt %) |
| PVOH | 0.97 | 0.97 | 0.97 | 0.97 | 0.97 | 0.97 |
| Takenate ® D-110N[1] | 6.51 | 6.51 | 6.50 | 6.51 | 6.51 | 6.51 |
| Perfume[2] | 29.16 | 29.16 | 29.16 | 29.20 | 29.20 | 29.20 |
| Guanidine carbonate | 0.58 | 0.38 | 0.19 | 0.24 | 0.19 | 0.15 |
| Guanazole | 0.21 | 0.42 | 0.63 | 0.58 | 0.63 | 0.68 |
| Guanidine carbonate:Guanazole molar ratio | 75:25 | 50:50 | 25:75 | 18:82 | 15:85 | 11:89 |
| Water | 62.57 | 62.56 | 62.55 | 62.50 | 62.50 | 62.49 |

[1] Trimethylol propane-adduct of xylylene diisocyanate, origin: Mitsui Chemicals, Inc., Japan
[2] Perfuming composition made with the ingredients of Table 1

Control Capsules G to M

Control polyurea microcapsules G and H formed with only one polyamine and control polyurea microcapsules I to M formed with an aliphatic polyisocyanate were prepared following the general procedure with the following ingredients:

TABLE 3

| | Composition of Capsules G to M | | | | | | |
| --- | --- | --- | --- | --- | --- | --- | --- |
| Ingredient | Capsules G Amount (wt %) | Capsules H Amount (wt %) | Capsules I Amount (wt %) | Capsules J Amount (wt %) | Capsules K Amount (wt %) | Capsules L Amount (wt %) | Capsules M Amount (wt %) |
| PVOH | 0.97 | 0.97 | 0.97 | 0.96 | 0.96 | 0.97 | 0.96 |
| Takenate ® D-110N[1] | 6.51 | 6.50 | 0 | 0 | 0 | 0 | 0 |
| Desmodur ® N-100[2] | 0 | 0 | 6.45 | 6.43 | 6.43 | 6.43 | 6.42 |
| Perfume[3] | 29.17 | 29.15 | 28.71 | 28.93 | 28.93 | 28.95 | 28.91 |
| Guanidine carbonate | 0.77 | 0 | 1.14 | 0.76 | 0.38 | 1.55 | 0 |
| Guanazole | 0 | 0.84 | 0.42 | 0.84 | 1.25 | 0 | 1.69 |

TABLE 3-continued

Composition of Capsules G to M

| Ingredient | Capsules G Amount (wt %) | Capsules H Amount (wt %) | Capsules I Amount (wt %) | Capsules J Amount (wt %) | Capsules K Amount (wt %) | Capsules L Amount (wt %) | Capsules M Amount (wt %) |
|---|---|---|---|---|---|---|---|
| Guanidine carbonate:Guanazole molar ratio | 100:0 | 0:100 | 75:25 | 50:50 | 25:75 | 100:0 | 0:100 |
| Water | 62.58 | 62.53 | 62.30 | 62.08 | 62.05 | 62.10 | 62.01 |

[1] Trimethylol propane-adduct of xylylene diisocyanate, origin: Mitsui Chemicals, Inc., Japan
[2] Biuret of hexamethylene diisocyanate; origin: Bayer
[3] Perfuming composition made with the ingredients of Table 1

Example 2

Olfactive Performance of Capsules According to the Invention Compared with Control Capsules
Procedure for Microcapsules Deposition on Cotton
A square of cotton fabric (12 cm×12 cm) was cut. A deposit zone was delimited in form of 10 centimeters diameter circle. For each capsule, four samples were analyzed in order to obtain a statistic measurement. Each dispersion of microcapsules was diluted 100 times in water. Diluted dispersion (1 g) was deposited into the circle on the fabric, from the edges to the center. Fabric was left to dry for 24 h.
Measurement of Perfume Release after Rubbing
AFFIRM® is a single quadrupole mass spectrometer fitted with an APCI (atmospheric chemical ionisation source and an MS-Nose interface). The operating parameters used throughout the course of these experiments are given below.

| Source Temperature | 105° C. |
|---|---|
| Heated transfer line | 150° C. |
| Heated Nitrogen transfer line | 105° C. |
| Sampling flow rate | 50 mL/min |
| Source gas flow rate | 10 L/min |
| Ionisation voltage | 3.8 kV |
| Cone voltage | 14 V |

Prior to rubbing, the sample was placed in a 1 L beaker and the headspace which was subsequently sealed with aluminum foil and allowed to equilibrate for 2 min. The foil was then pierced with the sampling probe of the MS-Nose and the headspace sampled for 1 minute (sampling flow rate 50 mL/min). The towel was then removed and rubbed 10 times under controlled conditions. Following the rubbing it was immediately placed in a second 1 L glass beaker and sealed again with aluminum foil and allowed to equilibrate for 2 minutes. The aluminum foil was then pierced with the MS-nose sampling probe and the headspace measured for 1 min. The fragrance release was determined by subtracting the initial (un-rubbed) measurement from the measurement after rubbing. Three replicates of each sample were carried out to determine the reproducibility. The results obtained from the headspace analysis after rubbing of the different samples are summarized in FIG. 1.

Figure 1:
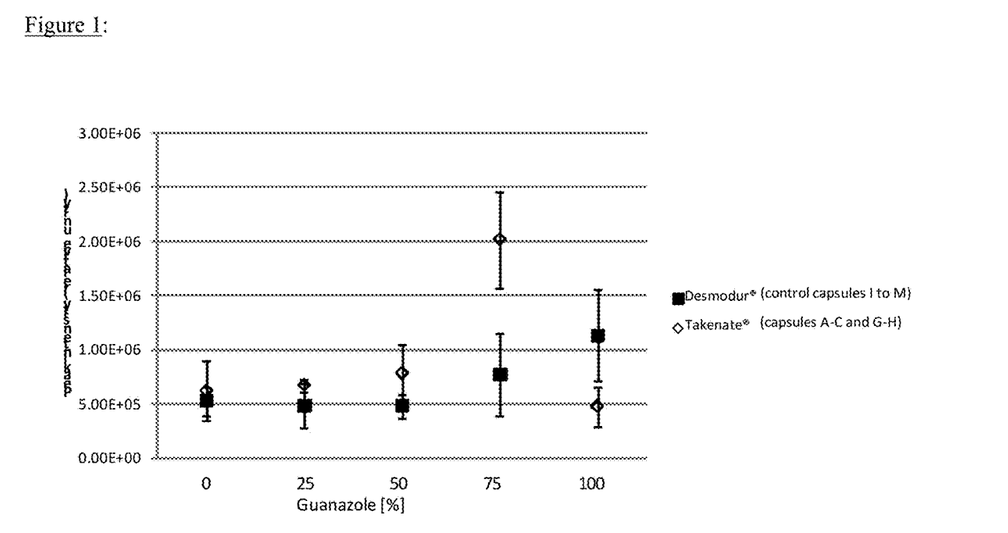
FIG. 1: Represents the release of perfume from microcapsules after rubbing as a function of the ratio between guanidine carbonate and guanazole measured by AFFIRM® (100% correspond to control microcapsules formed only with guanazole and 0% correspond to control microcapsules formed only with guanidine carbonate).
  Correspond to capsules A to C (invention) and control capsules G and H formed with an aromatic polyisocyanate
  Correspond to capsules I to M formed with an aliphatic polyisocyanate (control)

FIG. 1 shows a very important effect of the capsules shell composition on the intensity of perfume after rubbing. The combination of at least one aromatic polyisocyantes with a specific mixture of polyamines leads to capsules with great performance in term of perfume release. The capsules of the present invention (capsules A to C) unexpectedly outperform compared to control capsules (capsules G to M). In particular, a major effect is obtained using trimethylol propane-adduct of xylylene diisocyanate in combination with a mixture of guanidine carbonate and 3,5-diamino-1,2,4-triazole in a respective molar ratio of 25:75 (capsules C). So, the specific composition of the microcapsules according to the invention allows improving the olfactive performance of microcapsules of the present invention.

Figure 2:
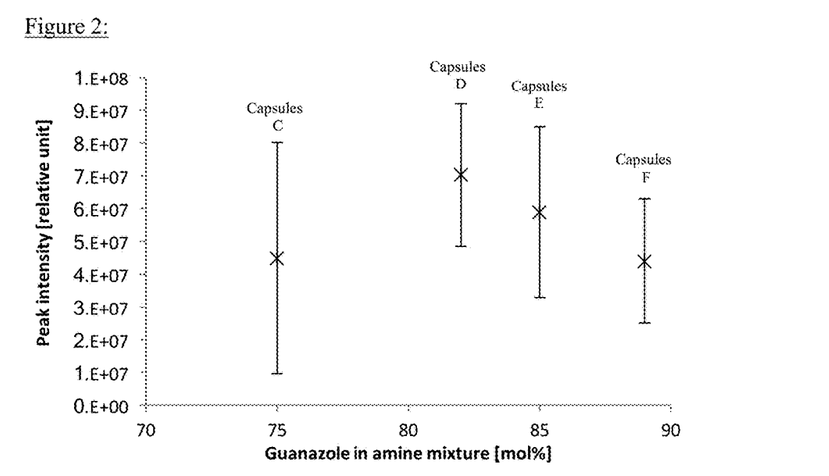
FIG. 2: Represents the release of perfume from microcapsules of the invention after rubbing as a function of the ratio between guanidine carbonate and guanazole measured by AFFIRM® (75% correspond to microcapsules formed with a Guanidine carbonate:Guanazole molar ratio of 25:75).

FIG. 2 illustrate the performance of various mixture of guanidine carbonate and 3,5-diamino-1,2,4-triazole with different molar ratios from 25:75 to 11:89 (Capsules C, D, E and F.

Example 3

Comparative Capsules Prepared According To a Process Described in US2013/0313734
Comparative Capsules 1 were Prepared as Follows
Polyisocyanate (Takenate® D-110N, 5.70 g) was diluted into a perfume oil (Table 1, 22.90 g) to form an oil phase. A solution of polyvinyl alcohol (Mowiol® 18-88, trademark from Kuraray, 1 wt %, 34.50 g) was prepared in water to form the aqueous phase. The oil and aqueous phases were mixed together, and then dispersed with Ultra Turrax for 2 min at 24 000 rpm. The resulting emulsion was put into a 250 mL glass double-jacketed reactor and agitated at 350 rpm. A solution of guanidine carbonate in water (15 wt %, 4.13 g) was added and the emulsion was warmed up to 70° C. and then kept at this temperature for 2 h. A solution of 3,5-diamino-1,2,4-triazole in water (20 wt %, 9.44 g) was added into the emulsion which was stirred at 70° C. for 4 hours. The reaction mixture was finally cooled down to room temperature.

Comparative Example 2 were Prepared as Follows
Polyisocyanate (Takenate® D-110N, 5.70 g) was diluted into a perfume oil (Table 1, 22.90 g) to form an oil phase. A solution of polyvinyl alcohol (Mowiol® 18-88, trademark from Kuraray, 1 wt %, 34.50 g) was prepared in water to form the aqueous phase. The oil and aqueous phases were mixed together, and then dispersed with Ultra Turrax for 2 min at 24 000 rpm. The resulting emulsion was put into a 250 mL glass double-jacketed reactor and agitated at 350 rpm. A solution of guanidine carbonate in water (15 wt %, 4.13 g) was added and the emulsion was warmed up to 70° C. and then kept at this temperature for 2 h. A solution of diethylenetriamine (origin: Aldrich, 99%) in water (20 wt %, 9.44 g) was added into the emulsion which was stirred at 70° C. for 4 hours. The reaction mixture was finally cooled down to room temperature.

Figure 3:
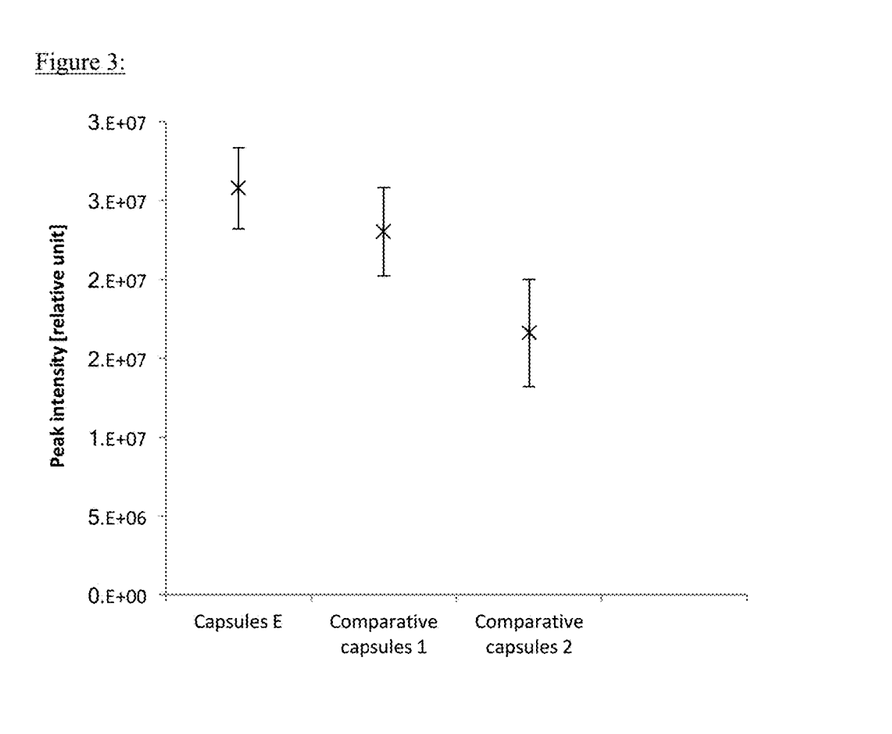
FIG. 3: Represents the release of perfume from microcapsules after rubbing of capsules E and comparative capsules 1 to 2 measured by AFFIRM®.

Performance of the comparative capsules measured by Affirm® is represented in FIG. 3 together with the performance of the capsules E according to the invention. Capsules E from the present invention demonstrate a better release of perfume after rubbing than the capsules prepared with protocol described in document US2013/0313734; i.e. successive addition of both polyamines, using as polyamines guanidine carbonate and 3,5-diamino-1,2,4-triazole (Comparative capsules 1, FIG. 3). Capsules E of the present invention work even better than the capsules prepared with protocol described in document US2013/0313734 using as polyamines reported in said document; i.e. guanidine carbonate and diethylenetriamine (Comparative capsules 2, FIG. 3).

Example 4

Figure 4:
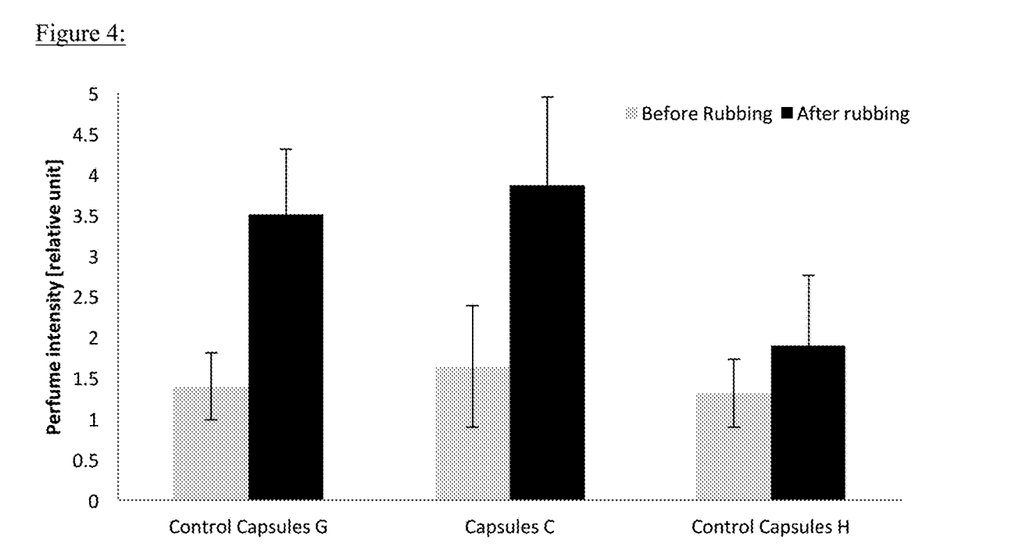
FIG. 4: Represents the release of perfume from microcapsules before and after rubbing of capsules E of the present invention compared to control capsules G and H determined by sensory analysis.

Olfactive Performance on Fabric of Capsules According to the Invention Compared with Control Capsules To mimic the final application, capsules were directly deposited onto pieces of cotton fabric. Perfume intensity after rubbing was measured by sensory analysis with panelists (n=7). FIG. 4 summarizes the results obtained with capsules C and control capsules G and H. The release upon rubbing is expressed as the perceived intensity on a scale from 1=no odor to 7=strong odor.

Dispersions of capsules C and control capsules G and H were diluted at 0.3 wt % and directly applied (1 g of dispersion) on the surface of cotton towels (Origin: Avana deluxe), which were dried for 24 h at room temperature. Perfume intensity was finally evaluated before and after rubbing of the towels (FIG. 4).

Results show that a higher intensity of perfume is perceived with the capsules C (3.9 out of 7) compared to control capsules G and H (3.5 and 1.9, respectively).

Example 5

Fabric Softener According to the Invention

A dispersion of capsules E (0.25 g) was formulated in a fabric softener conditioner (49.75 g), with the composition described below. Capsules were stirred with an incubator shaker (IKA KS 40000 is control, origin IKA) for 10 minutes.

| | |
|---|---|
| Stepantex ® VL90 A (origin: Stepan) | 16.5% by weight |
| Calcium chloride (10% aq. solution) | 0.6% by weight |
| Water | 82.9% by weight |

Example 6

Rinse-off Hair Conditioner According to the Invention

A dispersion of capsules E (0.25 g) was formulated in a rinse-off hair conditioner (49.75 g, formulation below), as described in Example 5.

| A | |
|---|---|
| Water deionized | 82.250% by weight |
| Chlorehexidine dihydrchloride | 0.050% by weight |
| Natrosol 250 H (hydroxycellulose) | 1.000% by weight |
| Dehyquart C 4046 (Cetearyl alcohol and dipalmitoylethyl hydroxyethylmonium methosulfate and ceteareth-20 | 0.200% by weight |
| Mirasil ADM-E (amodimethicone and trideceth-6 | 1.200% by weight |
| Genamin KDM (behentrimonium chloride) | 1.000% by weight |
| Crodamol SS (cetyl esters) | 0.500% by weight |
| Crodacol C 90 (cetyl alcohol) | 3.000% by weight |
| Myristyl Alcohol (alcohol C 14) | 0.200% by weight |
| B | |
| Water deionized | 10.000% by weight |
| Nipagim M (metyhlparaben) | 0.300% by weight |
| C | |
| Perfume | 0.300% by weight |

Example 7

Day Cream According to the Invention

A dispersion of capsules E (0.25 g) was formulated in a day cream (49.75 g, formulation below), as described in Example 5.

| A | |
|---|---|
| Arlacel ® 985 (origin: Atlas Powder Company) | 5.0% by weight |
| Cetyl alcohol (origin: Sigma-Aldrich) | 0.5% by weight |
| Tefose ® 2561 (origin: Gattefossé SA) | 4.0% by weight |
| Biolip P 90 (Squalan) (origin: Gattefossé SA) | 1.0% by weight |
| Mineral oil 30-40 CPS (Paraffin oil) | 2.0% by weight |
| Petroleum jelly (Petrolatum) (origin: Holler & Co GmbH) | 5.5% by weight |
| B | |
| Water (deionized) | 76.2% by weight |
| Propylene glycol | 5.0% by weight |
| C | |
| Nipaguard PO 5 (phenoxyethanol (and) piroctone olamine, origin: Clariant) | 0.6% by weight |
| D | |
| PNC 400 (sodium carbomer) (origin: 3 V International) | 0.2% by weight |

Example 8

Antiperspirant Roll-on Emulsion According to the Invention

A dispersion of capsules E (0.25 g) was formulated in antiperspirant roll-on emulsion (49.75 g, formulation below), as described in Example 5.

| A | |
|---|---|
| 1 BRIJ 72 (Steareth-2) | 3.250 wt % |
| 2 BRIJ 721 (Steareth-21) | 0.750 wt % |
| 3 ARLAMOL E (PPG-15 Stearyl Ether) | 4.000 wt % |
| B | |
| 4 WATER deionized | 51.000 wt % |
| C | |
| 5 LOCRON L (Aluminum Chlorohydrate 50% aqueous solution) | 40.000 wt % |
| D | |
| 6 PERFUME | 1.000 wt % |

The day cream was prepared according to the following protocol. Mixtures A and B were separately heated to 75° C.; Mixture A was then added to mixture B under stirring and the obtained mixture homogenizes for 10 minutes. Then, the obtained mixture was cooled down to room temperature still under stirring; Component C was then slowly added at 45° C., while keep mixing to room temperature, before adding component D at 35° C.

Example 9

Shower Gel According to the Invention

A dispersion of capsules E (0.25 g) was formulated in a shower gel (49.75 g, formulation below), as described in Example 5.

| | |
|---|---|
| Water deionised | 58.4 wt % |
| Carbopol ® Aqua CC | 8.0 wt % |
| (Polymer Polyacrylate-1 Crosspolymer, origin: Noveon) | |
| Citric Acid (40% aqueous solution) | 0.50 wt % |
| Zetesol AO 328 U | |
| Sodium C12-C15 Pareth Sulfate (Zschimmer & Schwarz) | 25.00 wt % |
| Tego ® Betain F 50 Cocamidopropyl Betaine | 4.00 wt % |
| (Goldschmidt AG) | |
| GlydantTM Plus Liquid DMDM Hydantoin | 0.10 wt % |
| and Iodopropynyl Butylcarbamate (Lonza) | |
| Sodium Chloride (20% aqueous solution) | 4.00 wt % |

Example 10

Performance of Capsules in a Fabric Softener

Capsules E and Comparative Capsules 2 were formulated in a fabric softener as described in Example 5. A fabric softener formulation (70.0 mg) and Capsules E (0.23 mg) were added in a beaker and diluted with water (23.3 mL). A piece of cotton fabric (5 g) was introduced in a beaker and the diluted fabric softener was added. The cotton fabric was stirred manually for 3 min and left for 2 min. It was finally wrung out to have a total weight of 10 g and dried overnight. The same protocol was applied to Comparative Capsules 2.

Figure 5:
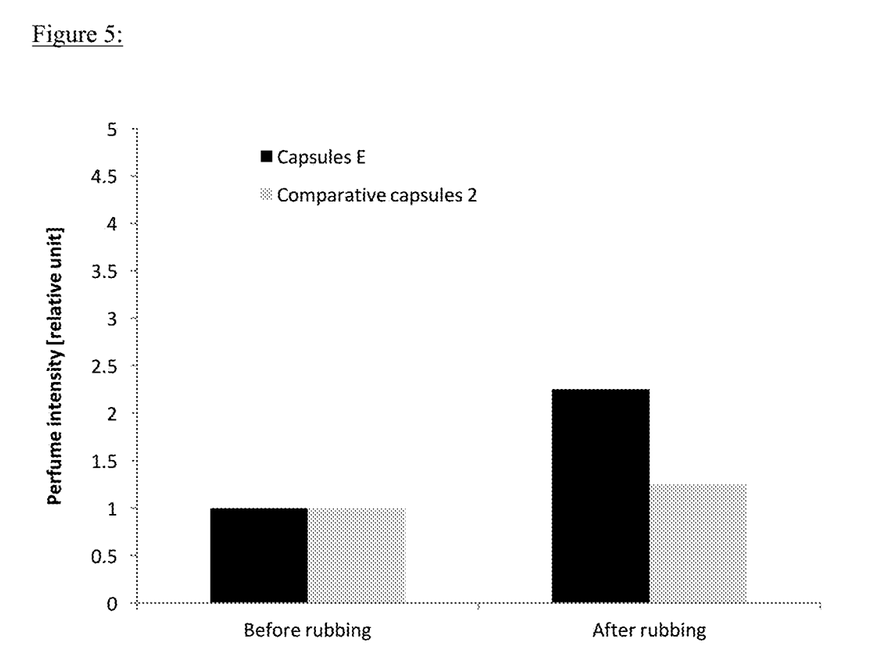
FIG. 5: Represents the release of perfume determined by sensory analysis from a fabric softener comprising microcapsules E of the present invention or comparative microcapsules 2 before and after rubbing of a tissue.

Perfume release was assessed by sensory analysis with panelists (n=4). Results shown in FIG. 5 illustrate that higher intensity of perfume was perceived with the capsules E (2.3 out of 7) compared to Comparative Capsules 2 (1.3).

What is claimed is:

1. A process for the preparation of polyurea microcapsules comprising the following steps:
   a) dissolving at least one aromatic polyisocyanate having at least two isocyanate groups in a perfume-containing oil to form an oil phase;
   b) dispersing the oil phase obtained in step a) into an aqueous solution comprising emulsifier to form an oil-in-water emulsion;
   c) adding to the oil-in-water emulsion obtained in step b) a mixture of guanidine and 3,5-diamino-1,2,4-triazole in a respective molar ratio from 30:70 to 10:90, to form a microcapsule slurry; and
   d) optionally drying the slurry.

2. The process according to claim 1, wherein the at least one aromatic polyisocyanate comprises trimethylol propane-adduct of xylylene diisocyanate.

3. The process according to claim 1, wherein the oil phase is devoid of any aliphatic polyisocyanate.

4. The process according to claim 1, wherein the at least one aromatic polyisocyanate consists of trimethylol propane-adduct of xylylene diisocyanate.

5. The process according to claim 1, wherein the emulsifier is polyvinyl alcohol.

6. Polyurea core-shell microcapsules comprising:
   a) an oil-based core comprising a perfume;
   b) a shell surrounding the core, the shell formed by interfacial polymerization of at least one aromatic polyisocyanate having at least two isocyanate groups and a mixture of guanidine and 3,5-diamino-1,2,4-triazole in a respective molar ratio from 30:70 to 10:90, to form a microcapsule slurry; and
   c) an emulsifier present on an inner surface of the shell.

7. A perfuming composition comprising
   a) as a perfuming ingredient, the polyurea microcapsules according to claim 6;
   b) at least one ingredient selected from the group consisting of a perfumery carrier, a perfumery co-ingredient, and a mixture thereof;
   c) optionally at least one perfumery adjuvant.

8. A perfuming consumer product comprising as a perfuming ingredient, the polyurea microcapsules according to claim 6.

9. The perfuming consumer product according to claim 8, wherein the consumer product is selected from the group consisting of: a perfume, a fabric care product, a body-care product, an air care product and a home care product.

10. The perfuming consumer product according to claim 8, wherein the perfumery consumer product is selected from the group consisting of: a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent and a hard-surface detergent.

11. A method of delivering perfume onto a surface or in the air, comprising treating the surface or the air with the microcapsules according to claim 6.

12. A perfuming consumer product comprising as a perfuming ingredient, the perfuming composition according to claim 7.

13. A method of delivering perfume onto a surface or in the air, which comprises treating the surface or the air with the perfuming composition according to claim 7.

14. The process according to claim 1, wherein guanidine and 3,5-diamino-1,2,4-triazole are in a respective molar ratio of 30:70 to 20:80.

15. The process according to claim 1, wherein the perfume is a liquid that is dissolved in a solvent other than an alcohol.

16. The polyurea microcapsules according to claim 6, wherein the perfume is a liquid that is dissolved in a solvent other than an alcohol.

17. The polyurea microcapsules according to claim 6, wherein guanidine and 3,5-diamino-1,2,4-triazole are present in a respective molar ratio from 30:70 to 20:80, prior to polymerization.

* * * * *